United States Patent
Nauflett et al.

(10) Patent No.: US 6,177,033 B1
(45) Date of Patent: Jan. 23, 2001

(54) NITRATION OF ORGANICS IN CARBON DIOXIDE

(75) Inventors: George W. Nauflett, Ft. Washington; Robert E. Farncomb, Accokeek, both of MD (US)

(73) Assignee: The United States of America as represented by the Secretary of the Navy

( * ) Notice: Under 35 U.S.C. 154(b), the term of this patent shall be extended for 0 days.

(21) Appl. No.: 09/334,555

(22) Filed: Jun. 21, 1999

Related U.S. Application Data

(60) Provisional application No. 60/137,223, filed on Jun. 1, 1999.

(51) Int. Cl.$^7$ ................................................ C06B 25/00
(52) U.S. Cl. .................................. 264/3.1; 149/109.6
(58) Field of Search ......................... 264/3.1; 149/109.6

(56) References Cited

U.S. PATENT DOCUMENTS

| | | |
|---|---|---|
| H447 | 3/1988 | Fischer et al. ............... 544/180 |
| H991 | 11/1991 | Fischer et al. ............... 549/510 |
| 4,432,902 | 2/1984 | McGuire et al. ........... 260/239 HM |
| 4,909,868 | 3/1990 | Melvin ............... 149/109.6 |
| 4,985,584 | 1/1991 | Millar et al. ............... 558/483 |
| 5,136,062 | 8/1992 | Millar et al. ............... 549/513 |
| 5,145,974 | 9/1992 | Paul et al. ............... 549/510 |
| 5,389,263 | 2/1995 | Gallagher et al. ........... 210/729 |
| 5,886,293 | 3/1999 | Nauflett et al. ............... 149/109.6 |

OTHER PUBLICATIONS

"Energetic Ingredients Processing in Liquid Carbon Dioxide" by Farncomb, et al., Life Cycles of Energetic Materials Conference, Mar. 29–Apr. 1, 1998, pp. 1–9 (first published Jun. 22, 1998).

"Nitrations with $N_2O_5$ and Anhydrous $HNO_3$ in Liquid Carbon Dioxide" by Nauflett, et al., JANNAF Conference, Apr. 1998, pp. 1–13.

*Primary Examiner*—Leo B. Tentoni
(74) *Attorney, Agent, or Firm*—Mark Homer

(57) ABSTRACT

Liquid or supercritical carbon dioxide is used to create an environment for forming nitrating agents and energetic materials.

18 Claims, 4 Drawing Sheets

NITRATION OF ORGANICS IN CARBON DIOXIDE

This application claims the benefit of Application Ser. No. 60/137,233, filed on Jun. 1, 1999.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention relates generally to producing energetic materials in a carbon dioxide environment. More specifically, the carbon dioxide environment is comprised of a supercritical and/or liquid carbon dioxide environment to form nitrating compounds and/or nitrate substrate materials into energetic materials. Most particularly, the present invention forms nitrogen pentoxide in a carbon dioxide environment that nitrates an appropriate substrate to an energetic material. The liquid carbon dioxide environment provides a nontoxic medium that acts as a heat sink for the chemical reaction occurring therein, and a separation medium for the resulting nitrated chemical compositions.

2. Brief Description of the Related Art

The synthesis and processing of energetic materials, in many cases, require that low temperatures be used. Selective nitration of materials with acid-sensitive moieties are commonly performed with $N_2O_5$ at low temperature in halogenated solvents. U.S. Pat. No. 4,985,584 (Millar et al.) discloses a process for the production of high energy materials using inert solvents such as a chlorinated alkane, while U.S. Pat. No. 5,136,062 (Millar et al.) discloses a method for the preparation of nitrate esters of epoxy alcohols in an inert organic solvent using halogenated alkanes such as $C_1$-$C_2$ chloroalkanes and $C_1$-$C_2$ chlorofluoroalkanes. U.S. Pat. No. 5,145,974 (Paul et al.) discloses the preparation of nitratoalkyl-substituted cyclic esters using $N_2O_5$ in an organic solvent, such as a $C_1$-$C_2$ chloroalkane of carbon tetrachloride, chloroform, methylene chloride, ethylene dichloride and dichloromethane. These compounds are toxic solvents, volatile organic compounds (VOC), ozone depleting substances (ODS), and/or hazardous air pollutants (HAP). In view of the foregoing, there is a need for a solvent that provides environmentally benign synthesis and processing methodologies for energetic materials manufacturing.

SUMMARY OF THE INVENTION

The present invention includes a process for manufacturing energetic materials comprising the steps of forming a carbon dioxide environment having a pressure of from about 500 psi or greater and a temperature of from about -30° C. or greater and producing an energetic material in the formed carbon dioxide environment.

The present invention further includes an apparatus for producing an energetic material comprising a first stage for combining a nitrating composition into a carbon dioxide environment having a pressure of from about 500 psi or greater and a temperature of from about -30° C. or greater, and a second stage for mixing the combined nitrating composition in the carbon dioxide environment with a substrate, wherein the substrate is nitrated.

DETAILED DESCRIPTION OF THE PREFERRED EMBODIMENT

The present invention relates generally to producing energetic materials in a supercritical/liquid carbon dioxide environment. The carbon dioxide environment is used to form the nitrating compounds, such as dinitrogen pentoxide, and/or allow the nitrating compounds to nitrate substrates into energetic materials. The process and apparatus of the present invention utilize the carbon dioxide environment to permit the manufacture of these energetic materials.

The process for manufacturing energetic materials includes the steps of forming a carbon dioxide environment having a pressure of from about 500 psi or greater and a temperature of from about -30° C. or greater, and producing an energetic material in the formed carbon dioxide environment.

As a solvent replacement for halogenated hydrocarbons such as methylene chloride, the liquid carbon dioxide (L-$CO_2$) environment provides several advantages to the manufacture of energetic materials. As a non-toxic medium, carbon dioxide is a nonregulated composition as a waste product by local, states, and federal environmental agencies. When used, carbon dioxide provides an economical solvent that may be derived from a numerous sources, including natural wells or from industrial processes as a by-product. Additionally, the non-flammable carbon dioxide solvent acts as a heat sink for the nitrations therein, and a separation medium for the resulting chemical compositions. $CO_2$ is considered extremely safe in relation to other possible solvents for producing energetic materials.

Figure 1A:
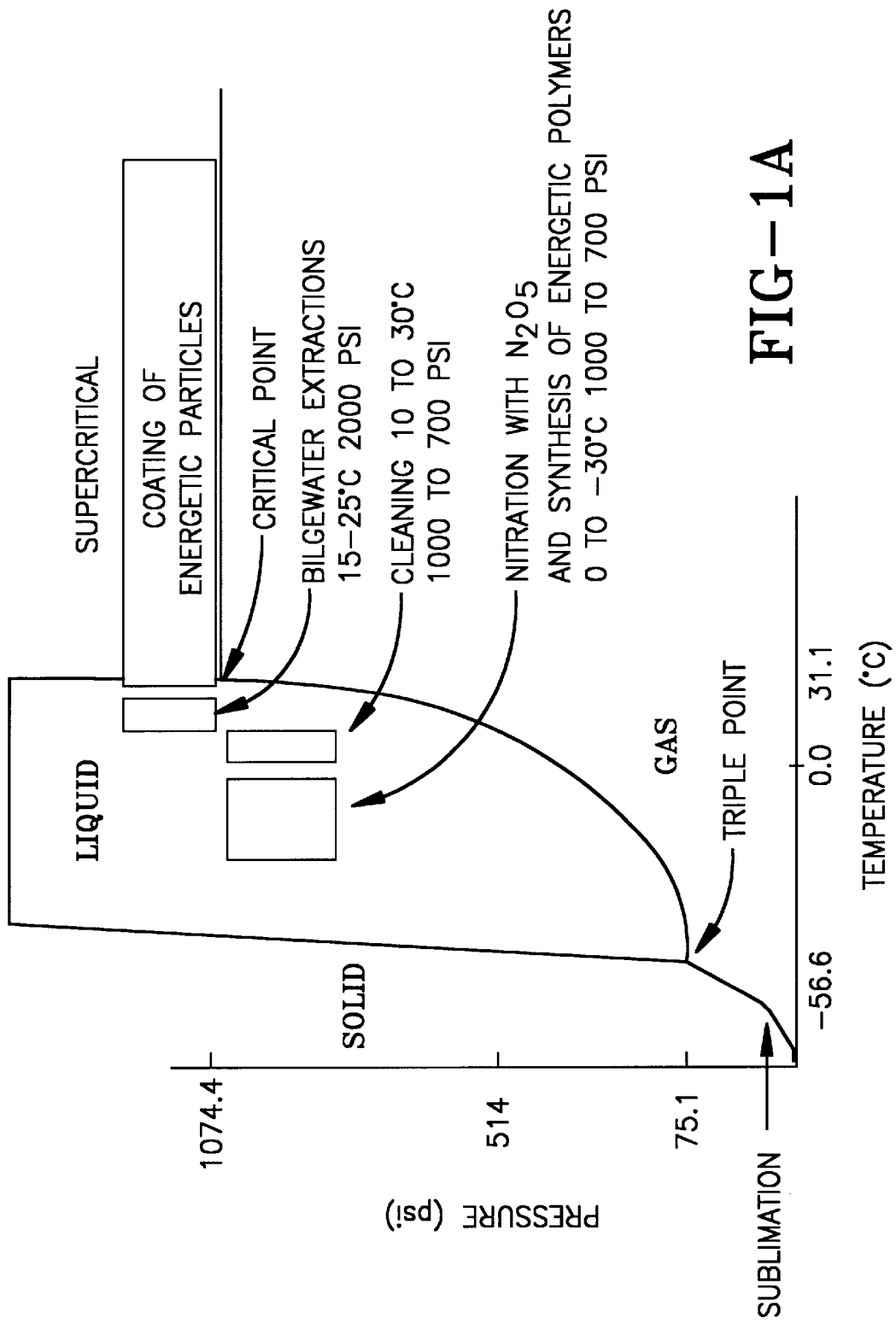
FIG. 1A is a phase diagram for carbon dioxide.
Figure 1B:
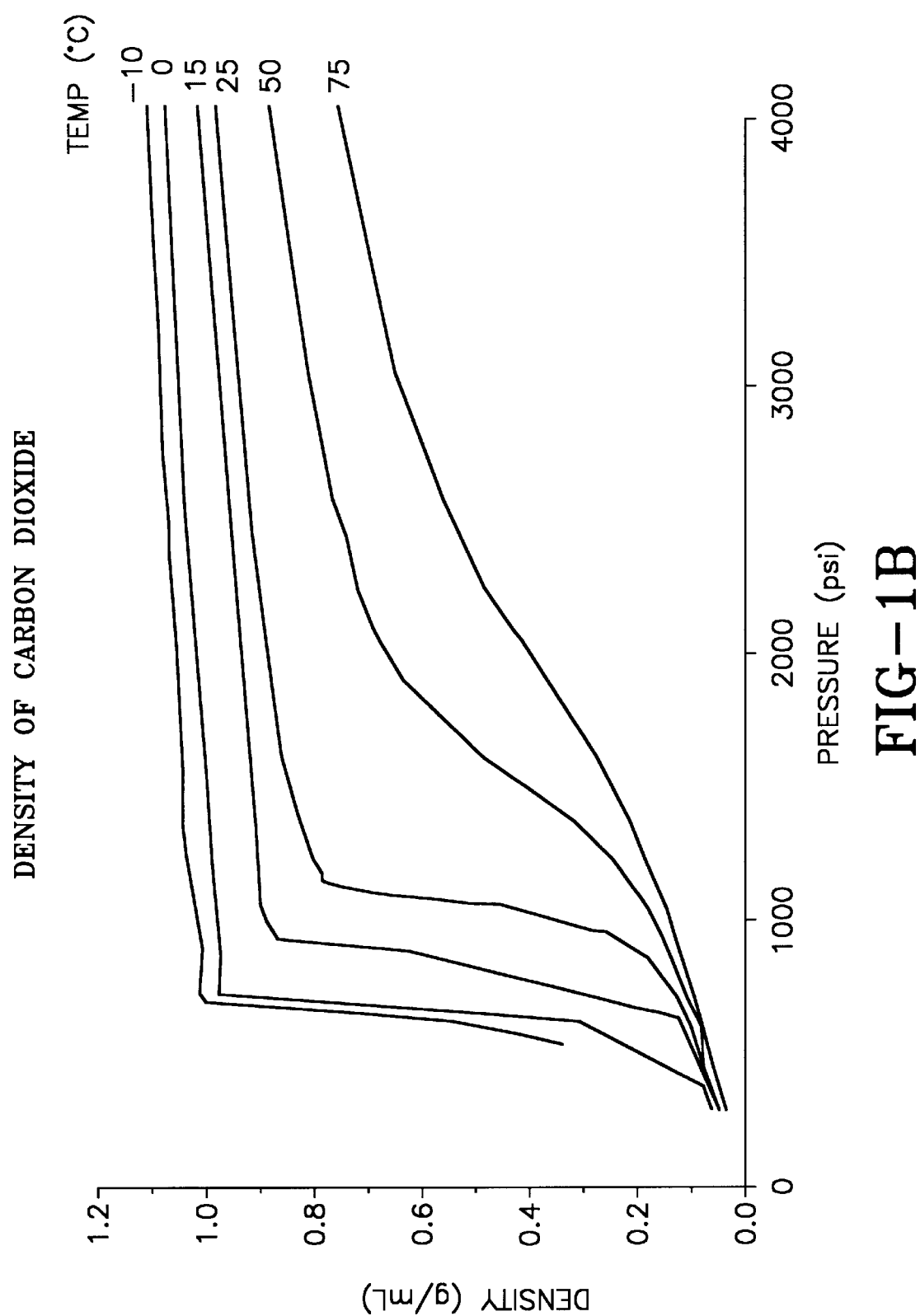
FIG. 1B illustrates carbon dioxide densities for temperatures of -10° C. through 75° C. and pressures of 200 psi through 4,000 psi.

FIG. 1A shows a phase diagram for carbon dioxide and FIG. 1B illustrates carbon dioxide densities for temperatures of -10° C. through 75° C. and pressures of 200 psi through 4,000 psi. The triple point of carbon dioxide is -56° C. and 5 stm (75 psi) and its critical point is 31.1° C. and 73 atm (1074 psi). L-$CO_2$ exists when the pressure and temperature are above the triple point, and either or both the temperature and pressure are below the critical point. Temperatures of from about -30° C. to about 0° C. provide a liquid carbon dioxide environment suitable for nitrating a substrate, with temperatures of from about 0° C. to about 31° C. providing additional flexibility in nitrating certain substrates while allowing greater ease in handling and maintaining environmental conditions. Supercritical carbon dioxide environments are obtained under appropriate pressures with temperatures of from about 31° C. or greater. Temperatures of from about 31° C. to about 80° C. are particularly useful for nitrating environments. Pressures useful within the process and apparatus of the present invention range from about 500 psi or greater to provide an adequate liquid and/or supercritical carbon dioxide environment. Liquid carbon dioxide environments are formed in ranges of from about 500 psi to about 1070 psi, with pressures for liquid carbon dioxide environments preferably from about 500 psi to about 1000 psi, and more preferably with pressure of from about 700 psi to about 1000 psi. Supercritical carbon dioxide environments are obtained at pressures of from about 1070 psi or greater.

Carbon dioxide ($CO_2$) in either a liquid or supercritical fluid provides the advantages of an inert solvent with the added capability of being readily separated from the nitrated compounds when the solvent is changed to gaseous $CO_2$. $CO_2$, which exists as a gas under ambient conditions, undergoes a gas-to-liquid phase change when confined and compressed to a pressure of 830 psig or greater at ambient temperature. With an increase of pressure and temperature of the L-$CO_2$ to 1058 psig and 31.3° C. or greater, respectively, supercritical $CO_2$ is obtained. Under supercritical conditions, the physical properties of $CO_2$ are intermediate between those of a liquid and a gas. Like a gas, supercritical $CO_2$ expands to fill its container, however, its density approximates that of a liquid. A solvent density close to the density of the substrate being processed is desirable.

Substrates nitrated within the process and apparatus of the present invention include any appropriate substrate for forming an energetic material. Substrates may be in either a liquid and/or solid phase. Suitable substrates include aromatic hydrocarbons, nitratable polymers, celluloses, sugars, alcohols, amines, and other known compounds in the art of energetic materials capable of being nitrated. Exemplary substrates of the present invention include polyols such as 3-methyl-3-oxetane-methanol, poly(3-methyl-3,oxetane-methanol), glycidol, γ-cyclodextrin, and cotton linters. Selection of the proper substrate to be nitrated varies to particular circumstances, with the type of substrate determinable by those skilled in the art.

The production of the energetic materials within the carbon dioxide environment may singularly comprise nitration of the substrate, and/or the formation of the nitrating agent within the carbon dioxide environment. Preferred nitrating compounds include dinitrogen pentoxide ($N_2O_5$), anhydrous nitric acid ($HNO_3$), and admixtures thereof. Other suitable nitrating compounds may be used, if desired. Preferably dinitrogen pentoxide is used. $N_2O_5$ is the anhydride of nitric acid and is a white, thermnally-labile, crystalline solid. In the pure solid state, $N_2O_5$ exhibits a half-life of 10 days at 0° C., and 10 hours at 20° C. The solid readily sublimes, having a vapor pressure of 51 mm at 0° C., 200 mm at 20° C., and one atmosphere at 32.5° C. The chemical properties of pure nitric acid include a specific gravity of 1.51, a melting point of −41.6° C., and a boiling point of 86° C.

Both $N_2O_5$ and anhydrous $HNO_3$ are soluble in L-$CO_2$, which allows the nitrating agents to be added in solution directly to the substrate being nitrated. The dinitrogen pentoxide may be formed in the carbon dioxide environment, after which a substrate capable of being nitrated is then placed into the carbon dioxide environment containing dinitrogen pentoxide. The process may be modified to place the substrate into a second carbon dioxide environment prior to placing the substrate into the carbon dioxide environment containing the dinitrogen pentoxide.

Formation of dinitrogen pentoxide within the carbon dioxide environment may occur with the dehydration of $HNO_3$ using a compound of phosphorous pentoxide ($P_2O_5$) or acetic anhydride, or with the ozonolysis of $N_2O_4$ with $O_3$. The use of L-$CO_2$ as a solvent for $N_2O_5$, $HNO_3$, acetic acid, and acetic anhydride offers significant safety and environmental benefits over conventional nitrating agents, such as mixed acid, to manufacture energetic materials. Nitric acid mixed with acetic acid or acetic anhydride can explode if not kept cold. L-$CO_2$ serves as a diluent for nitration reactions in an acetic anhydride/nitric acid media.

The preparation of dinitrogen pentoxide that includes dehydration of $HNO_3$ with phosphorous pentoxide, followed by distillation at 50° C. results in a product of unacceptable purity of approximately 30%, as illustrated in equation 1, below:

$$6\ HNO_3 + P_2O_5 \rightarrow 3\ N_2O_5 + 2\ H_3PO_4 \qquad (1)$$

However, $N_2O_5$ may be extracted with L-$CO_2$ at 0° C., since phosphoric acid and phosphorous pentoxide have little to no solubility in L-$CO_2$. The use of L-$CO_2$ extraction eliminates the need for distillation of $N_2O_5$. This results in an acceptable purity of the $N_2O_5$ within the present invention.

Other methods of producing dinitrogen pentoxide include the gas phase oxidation of $N_2O_4$, with ozone, as shown in equation 2, below:

$$N_2O_4 + O_3 \rightarrow N_2O_5 + O_2 \qquad (2)$$

The yields of the present invention for the reactions shown in equations 1 and 2 are from about 90% or more for systems designed for the extraction and processing of $N_2O_5$ with L-$CO_2$ at −10° C. The preferred method for the preparation of $N_2O_5$ is the gas phase oxidation of $N_2O_4$ with ozone, because the product is highly pure and no analysis is required.

Nitrations in L-$CO_2$ simplify solvent removal and purification of the formed energetic materials. After the nitration of the substrate, the energetic material is separated from the carbon dioxide environment. The L-$CO_2$ solvent evaporates on release of the pressure. As the L-$CO_2$ with the nitrated substrate enters a gaseous phase with the requisite pressure and temperature amounts, the gaseous $CO_2$ separates from the nitrated substrate. The gaseous $CO_2$ is either released or captured to be recycled, with L-$CO_2$ on the small scale batches generally vented to the atmosphere. The nitrated substrate remains in a liquid state and/or forms a solid state that is deposited within an appropriate container. Less waste is generated because $N_2O_5$ reacts instantly with water, eliminating the need for sulfuric acid. After the nitration has been completed, the nitrated product is washed with L-$CO_2$ eliminating the need to quench the reaction mixture with large volumes of water.

The nitration within L-$CO_2$/supercritical $CO_2$ systems have applications in the synthesis and processing of various energetic materials. O-Nitrations of liquids and solids were successfully performed using $N_2O_5$ and anhydrous $HNO_3$. Energetic materials formed from the present invention include those explosives typically manufactured with halogenated hydrocarbon solvents, such as ammonium dinitramide, nitrate esters (glycidol and methyl-3-oxetane-methanol). $N_2O_5$ and anhydrous nitric acid may be used in N-nitrations forming nitramines, ammonium dinitramide (ADN), cyclotrimethylenetrinitramine (RDX), tetranitrotet-raazocyclooctane (HMX), hexanitrohexazaisowurzitane (CL-20), and nitroanilines; C-nitrations forming trinitrotoluene (TNT) and bis(2,2-dinitropropyl formal/acetal 9BDNPF/a; and O-nitrations forming nitroglycerin (NG), 1,2,4-butanetrilltrinitrate (BTTN) and nitrocelluse (NC).

As $N_2O_5$, $HNO_3$, acetic acid and acetic anhydride are soluble in L-$CO_2$, the following exemplary sulfuric acid free reaction media are feasible for nitration:

$N_2O_5$ in L-$CO_2$ $N_2O_5$/$HNO_3$ in L-$CO_2$

Nitrations with $N_2O_5$ in 100% nitric acid, followed by L-$CO_2$ processing

Nitration with $HNO_3$/$Ac_2O$, followed by L-$CO_2$ processing

Examples of the nitration of a substrate include the nitration of 3-methyl-3-oxetanemethanol, shown in equation 3, below:

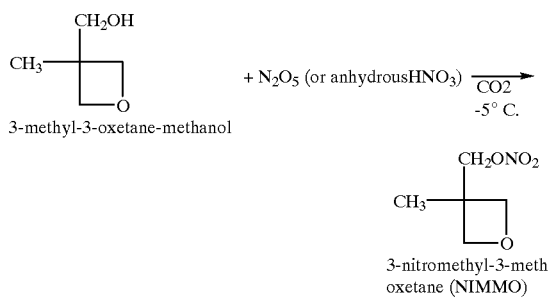

Other nitrations include forming HMX by the nitrolysis of 1,5-dinitro-3,7-diacetryl-1,3,5,7-tetraazacyclooctane and 1,3,5,7-tetraacetyl-1,3,5,7-tetraazaclooctane with $N_2O_5$ in 100% $HNO_3$ at from about 30° C. to about 35° C., shown in equation 4, below:

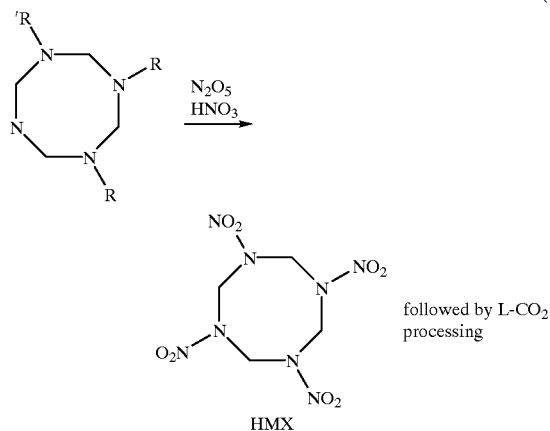

(4)

where $R=NO_2$ or acetyl and R'=acetyl. Or the preparation of ammonium dinitramide (ADN), shown in equation 5, below:

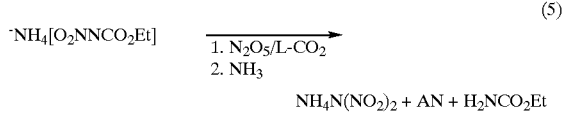

(5)

Figure 2A:
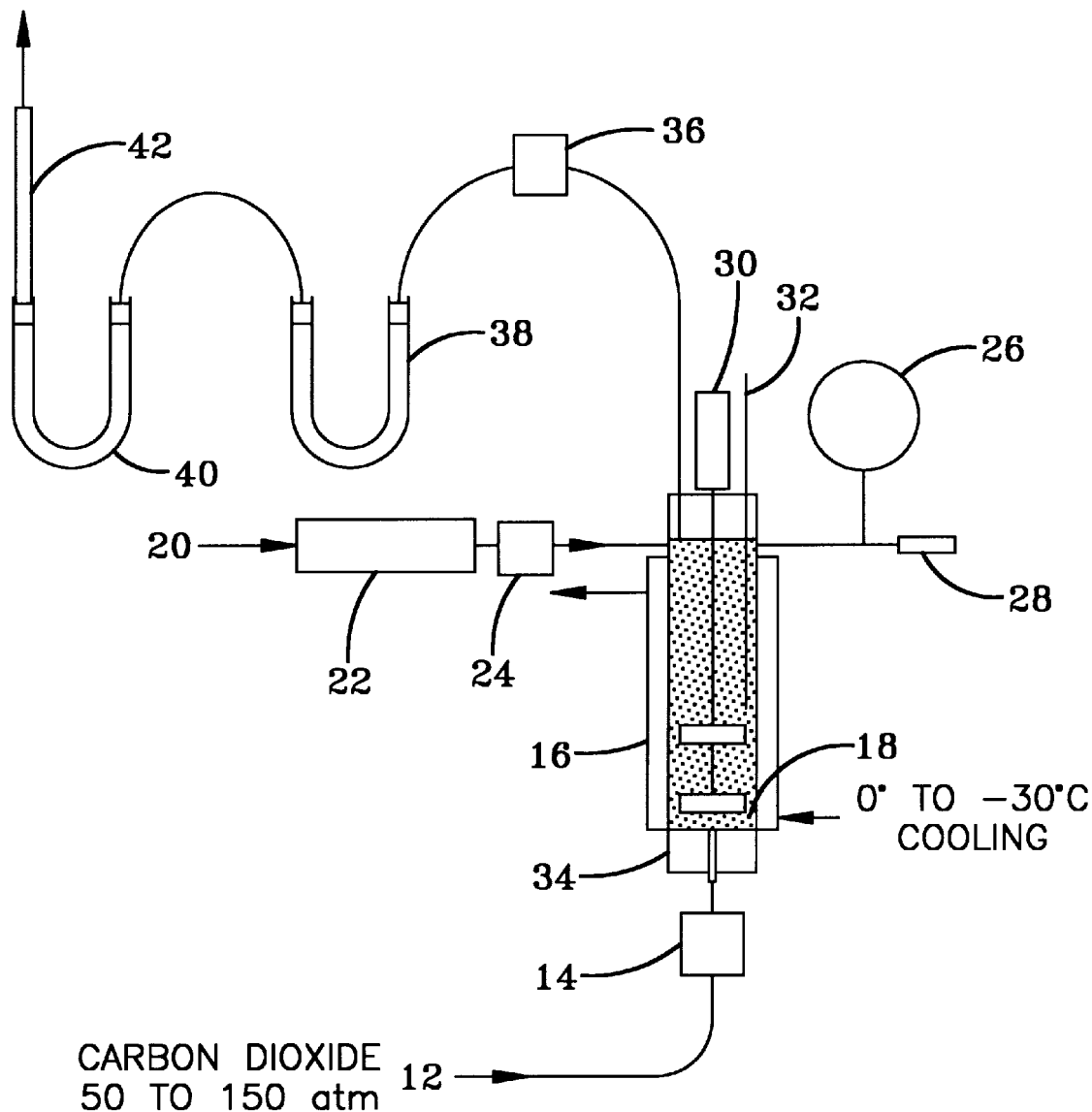
FIG. 2A shows an apparatus schematic diagram for the nitration of liquids in L-$CO_2$ with dinitrogen pentoxide; and, FIG. 2B shows an apparatus schematic diagram for the nitration of solids in L-$CO_2$ with dinitrogen pentoxide.

FIG. 2A shows a schematic diagram for the nitration of liquids in $L-CO_2$ with dinitrogen pentoxide. As seen in FIG. 2A, carbon dioxide 12 at a pressure of from about 50 to about 150 atmospheres enters through a value 14 into a 600-mL pressure vessel 34 with a cooling jacket 16 containing a nitrating agent 18 of $N_2O_5$ that is maintained at a temperature of from about 0° C. to about −30° C. The liquid substrate 20 to be nitrated is pumped through a valve 24 into the pressure vessel 34, where it is nitrated. A pressure relief mechanism having a pressure gauge 26 and rupture disk 28 is attached to the pressure vessel 34 to vent pressure as needed. A thermocouple 32 also is included to measure the temperature of the reaction. An agitator 30 having air motor with tachometer stirs the liquid substrate 20 and nitrating agent 18 within the pressure vessel 34 is used to maintain a uniform mixture of the nitrating agent 18 and liquid substrate 20. As liquid carbon dioxide soluble energetic material is formed, the energetic material is removed from the mixture through depressurization valve 36 and collected in U-tube 38. The carbon dioxide enters a second second U-tube 40 containing sodium carbonate for removal of acids from the carbon dioxide. The spent carbon dioxide is exhausted into the environment through flowmeter 42. Liquid carbon dioxide insoluble energetic material remains in vessel 34 and is removed after depressurization of the vessel 34.

Figure 2B:
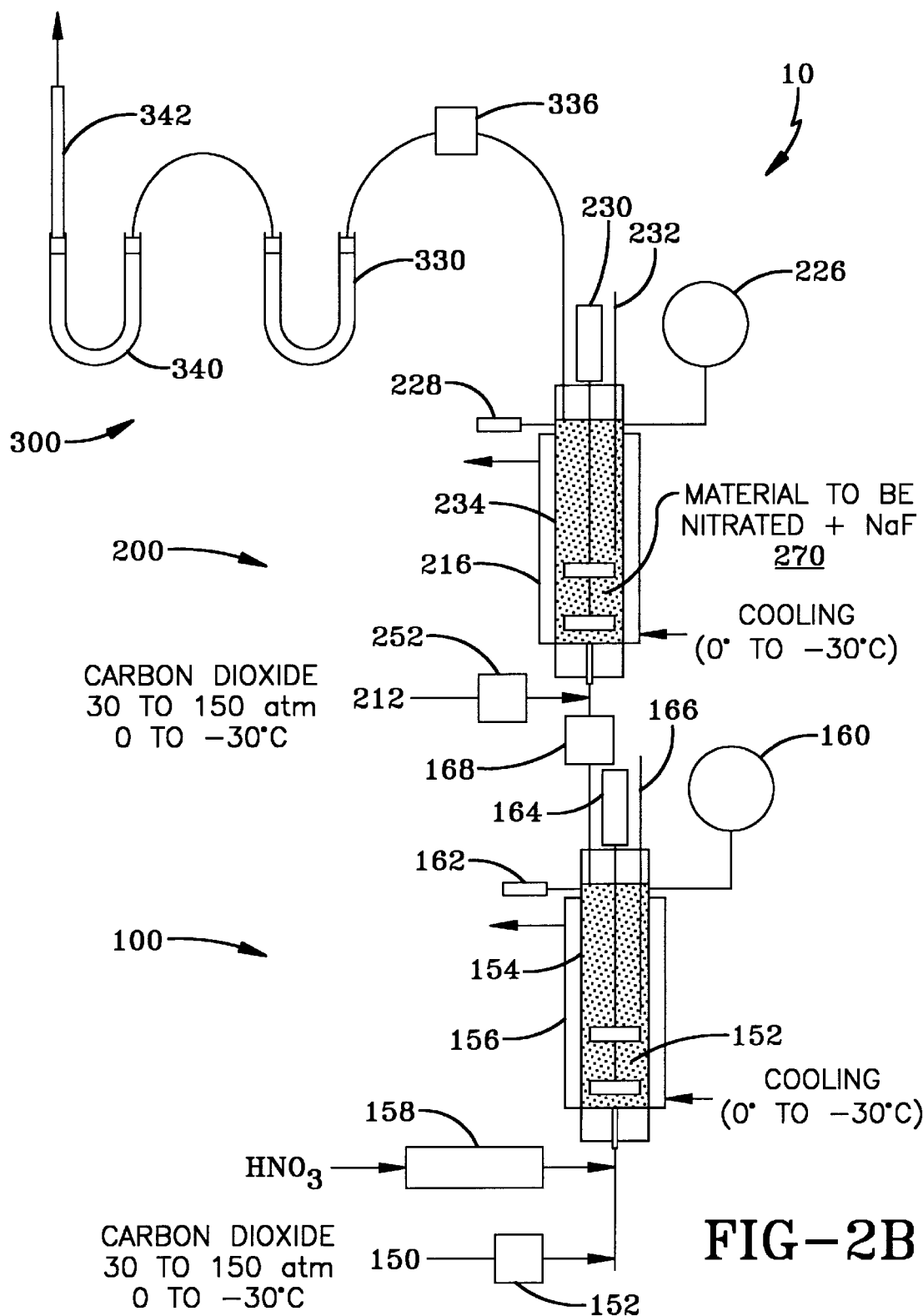

FIG. 2B shows a schematic diagram for the nitration of solid substrates in $L-CO_2$ with dinitrogen pentoxide within a second stage 200 of the apparatus 10, with the dinitrogen pentoxide being formed within a first stage 100 of the apparatus 10. As seen in FIG. 2B, the first stage 100 forms the nitrating agent in a carbon dioxide environment and the second stage 200 forms the energetic material from the nitrating agent in the carbon dioxide environment with the substrate. The first stage 100 includes the formation of the nitrating agent. In the first stage 100 carbon dioxide 150 at a pressure of from about 50 to about 150 atmospheres enters through a value 152 into a 600-mL pressure vessel 154 with a cooling jacket 156 containing a $P_2O_5$ or $H_2SO_4 \cdot SO_3$ 152 that is maintained at a temperature of approximately −25° C. Diatomaceous earth may be included as a processing aid. $HNO_3$ is added through a pump 158 into the pressure vessel 154, where it reacts to form dinitrogen pentoxide. A pressure relief mechanism having a pressure gauge 160 and rupture disk 162 is attached to the pressure vessel 154 to vent pressure if needed. An agitator 164 having air motor with tachometer stirs the dinitrogen pentoxide forming compounds within the pressure vessel 154 to maintain a uniform mixture. As dinitrogen pentoxide is formed, it is transported to the second stage 200 of the apparatus 10 through a valve 168. The second stage 200 nitrates the substrate. In a system similar to that shown in FIG. 2A, the second stage 200 includes combining carbon dioxide 212 at a pressure of from about 50 to about 150 atmospheres to the dinitrogen pentoxide at it enters into a 600-mL pressure vessel 234 with a cooling jacket 216 that maintains the vessel 234 at a temperature of approximately −25° C. The solid substrate 270 to be nitrated has been placed in the pressure vessel 234, where it is nitrated by the incoming nitrogen pentoxide. Sodium fluoride (NaF) may be added to complex nitric acid by-products. A pressure relief mechanism having a pressure gauge 226 and rupture disk 228 is attached to the pressure vessel 234 to vent pressure as needed. A thermocouple 232 also is included to measure the temperature of the reaction. An agitator 230 having air motor with tachometer stirs the solid substrate 270 and nitrating agent within the pressure vessel 234 to maintain a uniform mixture of the nitrating agent and solid substrate 220.

FIG. 2B further shows a third stage 300 where the formed energetic material is removed from the $CO_2$. Liquid carbon dioxide soluble energetic material is removed from the mixture through depressurization valve 336, and collected in U-tube 330. The carbon dioxide enters a second U-tube 340 containing sodium carbonate for removal of acids from the carbon dioxide. The spent carbon dioxide is exhausted into the environment through flowmeter 342. Liquid carbon dioxide insoluble energetic material remains in vessel 234 and is removed after depressurization of the vessel 234. Alternatively, the dinitrogen pentoxide may be formed within the first stage 100 of the apparatus 10 through ozonolysis of $N_2O_4$ received from a reservoir and reacted with $O_3$. The use of dinitrogen pentoxide, anhydrous nitric acid and carbon dioxide, at 50 to 140 atmospheres, requires special handling techniques to ensure safe processing of the chemical compositions, with the degree of safety needed being determinable by those skilled in the art. Nitration of substrates with acid-sensitive moieties performed with $N_2O_5$ at low temperatures in $L-CO_2$ as nitrating agent is clean, versatile, and offers significant environmental benefits.

In the following examples, liquid carbon dioxide ($L-CO_2$) was used as the solvent in nitrations of 3-methyl-3-oxetane-methanol, glycidol, γ-cyclodextrin, and cotton linters with dinitrogen pentoxide ($N_2O_5$) and/or anhydrous nitric acid. With substrates possessing both strained rings and labile groups, the reaction may be "fine-tuned" using $L\text{-}CO_2$. Because nitrate esters are acid-sensitive, sodium fluoride was used to complex with the nitric acid resulting from the nitration with $N_2O_5$.

A black coating may form on the stainless steel parts of the apparatus the first time the equipment is used for $N_2O_5$ nitration in $L\text{-}CO_2$ which does not change after subsequent nitrations.

EXAMPLES 1–3

The monomer 3-methyl-3-oxetane-methanol was nitrated with both $N_2O_5$ and anhydrous nitric acid as shown in equation 3, using $L\text{-}CO_2$ as the processing solvent, producing the monomer 3-nitratomethyl-3-methyl oxetane (NIMMO). The 3-nitratomethyl-3-methyl oxetane (NIMMO) was subjected to polymerization conditions in liquid carbon dioxide ($L\text{-}CO_2$), using gaseous boron trifluoride ($BF_3$) catalyst. The NIMMO contained approximately 9.3% nitrogen (9.5% theoretical).

EXAMPLE 1

The monomer 3-methyl-3-oxetane-methanol was nitrated with $N_2O_5$ in 20 gram batches with 10% excess nitrating agent at a temperature of –10° C. and a pressure of 68 atmospheres in $L\text{-}CO_2$ as the processing solvent. The yield was 95%.

EXAMPLE 2

The monomer 3-methyl-3-oxetane-methanol was nitrated with anhydrous nitric acid in 20 gram batches with 10% excess nitrating agent at a temperature of –10° C. and a pressure of 68 atmospheres in $L\text{-}CO_2$ as the processing solvent. The yield was 72%.

EXAMPLE 3

Poly(3-methyl-3-oxetane-methanol) was nitrated with $N_2O_5$ in 20 gram batches with 10% excess nitrating agent at a temperature of –10° C. and a pressure of 68 atmospheres in $L\text{-}CO_2$ as the processing solvent. The yield was 90%.

EXAMPLE 4

Glycidol was nitrated with $N_2O_5$ in 20 gram batches with 10% excess nitrating agent at a temperature of –10° C. and a pressure of 68 atmospheres in $L\text{-}CO_2$ as the processing solvent. The yield was 90%.

EXAMPLES 5–8

γ-Cyclodextrin (γCD) is a macrocycle containing eight glucose residues connected by alpha 1,4-glycosidic linkages having a molecular weight of 1297 and 24 hydroxyl groups. γCD was nitrated with both $N_2O_5$ and anhydrous nitric acid using $L\text{-}CO_2$ as the processing solvent, producing γ-Cyclodextrin nitrate (γCDN). Better yields and 13.5% nitrogen were obtained when sodium fluoride was used during the nitration. Sodium fluoride complexes with the by product nitric acid by hydrogen bonding. The nitric acid-sensitive γCDN was protected by the sodium fluoride/nitric acid complex. The yields of γCDN demonstrate the benefit of using sodium fluoride during the nitrations. The γCDN typically contained 13.5% nitrogen (14% theoretical) and the Differential Scanning Calorimeter (DSC) has an exotherm (3,090 joules/g) at 192° C.

EXAMPLE 5

γ-Cyclodextrin (γCD) was nitrated with $N_2O_5$ in 20 gram batches with 10% excess nitrating agent and NaF at a temperature of –10° C. and a pressure of 68 atmospheres in $L\text{-}CO_2$ as the processing solvent. The yield was 91%.

EXAMPLE 6

γ-Cyclodextrin (γCD) was nitrated with anhydrous nitric acid in 20 gram batches with 10% excess nitrating agent and NaF at a temperature of –10° C. and a pressure of 68 atmospheres in $L\text{-}CO_2$ as the processing solvent. The yield was 38%.

EXAMPLE 7

γ-Cyclodextrin (γCD) was nitrated with $N_2O_5$ in 20 gram batches with 10% excess nitrating agent at a temperature of –10° C. and a pressure of 68 atmospheres in $L\text{-}CO_2$ as the processing solvent. The yield was 45%.

EXAMPLE 8

γ-Cyclodextrin (γCD) was nitrated with anhydrous nitric acid in 20 gram batches with 10% excess nitrating agent at a temperature of –10° C. and a pressure of 68 atmospheres in $L\text{-}CO_2$ as the processing solvent. The yield was 12%.

EXAMPLE 9

Cotton Linters were nitrated with $N_2O_5$ in 20 gram batches with 10% excess nitrating agent and NaF at a temperature of –10° C. and a pressure of 68 atmospheres in $L\text{-}CO_2$ as the processing solvent. The yield was 85%.

EXAMPLE 10

Nitramines are commonly prepared by the reaction of secondary amides with nitric acid in a dehydrating media such as acetic anhydride, by the addition of nitrate salts of secondary amines to acetic anhydride in the presence of a chloride ion catalyst, or by direct interaction of an amine with $N_2O_5$. Nitramines such as HMX are unstable in nitrating media containing sulfuric acid. $N_2O_5$ in $HNO_3$ is a useful reagent for the nitrolysis of various substituted amines to nitramines. HMX could be prepared by the nitrolysis of 1,5-dinitro-3,7-diacetryl-1,3,5,7-tetraazacyclooctane and 1,3,5,7-tetraacetyl-1,3,5,7-tetraazaclooctane with $N_2O_5$ in 100% $HNO_3$ at a temperature of from about 30° C. to about 35° C. in supercritical $CO_2$ with yields of from about 79% to about 98% obtainable, as shown in equation 4 above.

EXAMPLE 11

Ammonium dinitramide (ADN) could be prepared in 80% yield using a 15% $N_2O_5$ solution in $L\text{-}CO_2$, as shown in equation 5 above.

EXAMPLE 12

Nitration of a liquid using $N_2O_5$ in $L\text{-}CO_2$: Preparation of Nitrotomethyl methyl oxetane (NIMMO). Solid $N_2O_5$ (11.3 g, 0.104 mol) was added to the nitration vessel, and the temperature was lowered to 3° C. by circulating ice water through the jacket. At a pressure of 170 atm, 3-hydroxymethyl-3-methyl oxetane (3M3 OM: 9.5 g, 0.094 mol) was pumped into the vessel at 0.5 mL/min. and at 2±0.5° C., while agitating at 250 rpm. The resulting NIMMO was removed from the reaction vessel with supercritical $CO_2$. The yield of NIMMO was calculated to be 97% (based on NIMMO MW), and was found to contain ca. 2% of a mixture of dimers and trimers.

EXAMPLE 13

Nitration of a solid using $N_2O_5/L\text{-}CO_2$: Preparation of γ-Cyclodextrin Nitrate (γCDN). γCD (20 g, 0.015 moles)

was added to the 600-mL vessel. $N_2O_5$ (44 g, 0.407 moles, 10 mole % excess) was added to the 60-mL vessel. The agitator was turned on and carbon dioxide was slowly added to both vessels until the pressure was 68 atm (1,000 psi). Cooling fluid at −25° C. was pumped through the jackets of both vessels. The 600-mL vessels $CO_2$ addition valve was closed and the valve between the two vessels was opened. For 145 minutes, 1.4 grams of $CO_2$/minute was passed through the two vessels. The temperature was −5±0.2° C. The pressure was slowly released, and the product was poured into a 2-L beaker containing sodium bicarbonate (80 g, 0.95 mL). The mixture was filtered and the γCDN was washed twice with water (0.7 L). The yield of γCDN was 91% (26.5 g) and the nitrogen content was 13.5%. The DSC had an exotherm (3,090 joules/g) at 192° C.

EXAMPLE 14

Nitration of 3-hydroxymethyl-3-methyl oxetane with anhydrous $HNO_3$ in $L-CO_2$: Anhydrous nitric acid (41 g, 0.65 mol, 20% excess) was added to the 600-mL vessel. Carbon dioxide was added with cooling until the pressure was 68 atm (1,000 psi) at −5° C. With the agitator turning at 170 rpm, 3-hydroxymethyl-3-methyl oxetane (55 g, 0.54 moles) was pumped into the nitration vessel at 1 mL/min. At end of the addition the pressure was 163 atm (2,400 psi) and the temperature was −3° C. The pressure was released and extra carbon dioxide was added to flush the oxides of nitrogen from the product. The equipment was modified, the bottom outlet valve was connected to a 500-mL 2-neck flask, and 10 atm carbon dioxide added to the top. The product was transferred to the 500-mL 2-neck flask by opening the bottom outlet valve with the vessel under 10 atm. The NIMMO was washed with 8% sodium bicarbonate solution, water, and was dried. A yield of 57 g of a brown viscous oil was obtained (calculated 72% based on NIMMO MW). This NIMMO contained 9.3% nitrogen (9.5% theoretical).

EXAMPLE 15

NIMMO and γCDN: The monomer, 3-methyl-3-oxetane-methanol were separately nitrated with dinitrogen pentoxide ($N_2O_5$), anhydrous $HNO_3$ and also an admixture of $N_2O_5$ and $HNO_3$ as shown in eq. 5 using $L-CO_2$ as the processing solvent producing the monomer 3-nitratomethyl-3-methyl oxetane (NMNMO). The corresponding nitration of γCD produced γCDN.

The foregoing summary, description, examples and drawings of the invention are not intended to be limiting, but are only exemplary of the inventive features which are defined in the claims.

What is claimed is:

1. A process for manufacturing energetic materials, comprising the steps of:
   forming a carbon dioxide environment having a pressure of from about 500 psi or greater and a temperature of from about −30° C. or greater; and,
   producing an energetic material in the formed carbon dioxide environment.

2. The process of claim 1, wherein the step of forming a carbon dioxide environment comprises a liquid carbon dioxide environment.

3. The process of claim 1, wherein the step of forming a carbon dioxide environment comprises a supercritical carbon dioxide environment.

4. The process of claim 1, wherein the carbon dioxide environment comprises a temperature of from about −30° C. to about 0° C.

5. The process of claim 1, wherein the carbon dioxide environment comprises a temperature of from about 0° C. to about 31° C.

6. The process of claim 1, wherein the carbon dioxide environment comprises a temperature of from about 31° C. to about 80° C.

7. The process of claim 1, wherein the carbon dioxide environment comprises a pressure of from about 700 psi to about 1000 psi.

8. The process of claim 1, wherein the carbon dioxide environment comprises a pressure of from about 1070 psi or greater.

9. The process of claim 1, wherein the step of producing an energetic material comprises nitration of a substrate.

10. The process of claim 9, wherein the step of producing an energetic material comprises nitration of a substrate using a nitrating compound selected from the group consisting of dinitrogen pentoxide, anhydrous nitric acid, and admixtures thereof.

11. The process of claim 1, wherein the step of producing an energetic material comprises forming dinitrogen pentoxide with the dehydration of $HNO_3$ with a compound selected from the group consisting of $P_2O_5$ and acetic anhydride.

12. The process of claim 1, wherein the step of producing an energetic material comprises forming dinitrogen pentoxide with the ozonolysis of $N_2O_4$.

13. The process of claim 1, wherein the step of producing an energetic material comprises forming dinitrogen pentoxide in the carbon dioxide environment and then placing a substrate capable of being nitrated into the carbon dioxide environment with the formed dinitrogen pentoxide.

14. The process of claim 13, wherein the substrate is placed into a second carbon dioxide environment prior to placing the substrate into the carbon dioxide environment with the formed dinitrogen pentoxide.

15. The process of claim 1, wherein the produced energetic material comprises an explosive composition selected from the group consisting of ammonium dinitramide and nitramine.

16. The process of claim 1, further comprising the step of separating the produced energetic material from the carbon dioxide environment.

17. The process of claim 16, wherein the step of separating the produced energetic material from the carbon dioxide environment provides a carbon dioxide residue that is recycled.

18. A process for manufacturing energetic materials, comprising the steps of:
   forming a carbon dioxide environment having a pressure of from about 500 psi or greater and a temperature of from about −30° C. or greater; and,
   producing a nitrating agent in the formed carbon dioxide environment.

* * * * *